United States Patent [19]

Siddiqi et al.

[11] Patent Number: 4,859,306
[45] Date of Patent: Aug. 22, 1989

[54] SELECTIVELY ION-PERMEABLE DRY ELECTRODES FOR ANALYZING SELECTED IONS IN AQUEOUS SOLUTION

[75] Inventors: Iqbal Siddiqi, Geneva; Hans-Rudolf Wuhrmann, Lampenberg, both of Switzerland

[73] Assignee: Hoffman-La Roche Inc., Nutley, N.J.

[21] Appl. No.: 203,550

[22] Filed: May 31, 1988

Related U.S. Application Data

[63] Continuation of Ser. No. 942,110, Dec. 16, 1986, abandoned.

[30] Foreign Application Priority Data

Dec. 23, 1985 [CH] Switzerland ................. 5501/85

[51] Int. Cl.$^4$ .......................................... G01N 27/46
[52] U.S. Cl. ...................... 204/416; 204/91; 204/418; 204/419; 204/435
[58] Field of Search ............... 204/56.1, 91, 416–419, 204/435

[56] References Cited

U.S. PATENT DOCUMENTS

| | | | |
|---|---|---|---|
| 3,485,723 | 12/1969 | Nodeau et al. ............... | 435/4 |
| 3,819,488 | 6/1974 | Rush et al. .................. | 435/16 |
| 3,856,649 | 12/1974 | Genshaw et al. ............ | 204/418 |
| 4,053,381 | 10/1977 | Hamblen et al. ............ | 204/418 |
| 4,133,735 | 1/1979 | Afromowitz et al. ........ | 204/420 |
| 4,171,246 | 10/1979 | Hamblen et al. ............ | 204/418 |
| 4,184,936 | 1/1980 | Paul et al. ................... | 204/418 |
| 4,199,411 | 4/1980 | Kim ............................ | 204/418 |
| 4,199,412 | 4/1980 | Battaglia et al. ............ | 204/1 T |
| 4,214,968 | 7/1980 | Battaglia et al. ............ | 204/418 |
| 4,250,010 | 2/1981 | Kondo et al. ............... | 204/412 |
| 4,257,862 | 3/1981 | Schnipelsky et al. ........ | 204/400 |
| 4,271,265 | 6/1981 | Deneke et al. .............. | 435/16 |
| 4,272,328 | 6/1981 | Kim et al. ................... | 204/418 |
| 4,273,639 | 6/1981 | Gottermeier ................ | 204/418 |
| 4,282,079 | 8/1981 | Chang et al. ................ | 204/420 |
| 4,303,408 | 12/1981 | Kim et al. ................... | 204/418 |
| 4,314,895 | 2/1982 | Spaziani et al. ............. | 204/418 |
| 4,336,091 | 6/1982 | Gotter ........................ | 436/244.12 |
| 4,353,983 | 10/1982 | Siddiqi ....................... | 435/11 |
| 4,416,735 | 11/1983 | Kissel ......................... | 204/1 T |
| 4,451,339 | 5/1984 | Kranz et al. ................ | 204/91 |
| 4,454,007 | 6/1984 | Pace ........................... | 204/416 |
| 4,466,867 | 8/1984 | Habermann et al. ........ | 204/91 |
| 4,498,739 | 2/1985 | Itaya et al. .................. | 204/56.1 |
| 4,555,274 | 11/1985 | Kitajima et al. ............. | 148/240 |

FOREIGN PATENT DOCUMENTS

| | | |
|---|---|---|
| 29104 | 9/1980 | European Pat. Off. . |
| 85276 | 1/1982 | European Pat. Off. . |
| 83861 | 12/1982 | European Pat. Off. . |
| 1497240 | 10/1967 | France . |
| 2146816 | 3/1973 | France . |
| 2352300 | 12/1977 | France . |
| 2418462 | 2/1978 | France . |
| 7113260 | 3/1973 | Netherlands . |
| 604167 | 7/1981 | Switzerland . |
| 2102963 | 2/1983 | United Kingdom . |
| 2105043 | 3/1983 | United Kingdom . |
| 2106253 | 4/1983 | United Kingdom . |
| WO8001081 | 5/1980 | World Int. Prop. O. . |

OTHER PUBLICATIONS

Derwent Abstract 77-82983Y/47 corresponding to Swiss No. 604,167.
James et al., Anal. Chem., 44:856, (1972).
Moore, W., Physical Chemistry Prentice Hall Inc. 3rd Ed., London, p. 389, (1962).

Primary Examiner—T. Tung
Attorney, Agent, or Firm—Jon S. Saxe; Bernard S. Leon; A. Kate Huffman

[57] ABSTRACT

The electrode comprises an internal reference half-cell at stable potential comprising a conductive sheet, e.g. of metal of carbon, covered by a redox system. The redox system comprises a thin dehydrated layer of Prussian blue deposited by contact between the sheet and a mixture of alkaline ferrocyanide and a ferric salt.

4 Claims, 2 Drawing Sheets

SELECTIVELY ION-PERMEABLE DRY ELECTRODES FOR ANALYZING SELECTED IONS IN AQUEOUS SOLUTION

This application is a continuation of application Ser. No. 942,110, filed Dec. 16, 1986, now abandoned.

FIELD OF THE INVENTION

The invention relates to laminar electrodes comprising an ion selective diaphragm and used for determining certain ions in aqueous solution, e.g. $Na^+$, $K^+$, $Li^+$, $Ca^{+2}$, $Mg^{+2}$, $Cl^-$ and others, inter alia in biological fluids.

BACKGROUND OF THE INVENTION

There are already a large number of prior-art electrodes and similar devices for selectively determining ions in aqueous solutions. The electrodes usually comprise an internal electrochemical reference half-cell at a stable potential and adapted, in conjunction with an external reference electrode immersed simultaneously with the measuring electrode in a solution to be analyzed, to form a cell having a potential dependent on the presence of a given ion in the solution In some texts, an assembly of this kind comprising two electrodes and a connecting electrolyte is described as a "battery". We shall avoid using this term here, since a "battery" produces current in contrast to the present cell, which delivers a potential only.

The potential is proportional to the logarithm of the activity of the chosen ion in accordance with NERNST's well-known equation, one form of which, for example, is $E = E_o \pm K \ln C_i$ where $E_o$ is the standard potential and K is a constant. The potential is therefore proportional to the concentration of the ion, which can then be deduced by comparison with standard solutions.

For example, documents CH-A-604 167 and US-A-4 214 968; 4 053 381; 4 171 246 (EASTMAN KODAK) describe electrodes in the form of dry multi-laminates comprising, in the following order, an insulating support, a metal electrically conductive layer covered with an insoluble salt of the metal, a part of the layer being used as a terminal for connection to an electrometer, a layer of reference electrolyte in a hydrophilic binder and an ion-selective diaphragm for selectively measuring a given ion, to the exclusion of other ions in the analyzed substance. The assembly made up of the metal layer, the insoluble salt and the reference electrode constitutes the internal reference half-cell at stable potential. Alternatively the assembly can be replaced by a conductive layer covered with a redox system, e.g. the quinone-hydroquinone couple, which system likewise comprises an internal reference cell at stable potential.

The ionically selective diaphragm usually comprises a plasticizer and a hydrophobic matrix containing in dispersed form an ionophoric substance, i.e. one of use for selectively detecting a given ion to the exclusion of any other ions in the analyzed solution. The reference electrolyte layer comprises a suitable water-soluble salt dispersed in a hydrophilic binder matrix containing 5 to 25% water. Compare W. E. MORF et al., Ion-Selective Electrodes in Analytical Chemistry, Vol. I. FRIESER Editor, Plenum Press (1981). pp 221 ff.

Document US-A-3 856 649 (MILES) describes an electrode having a similar structure except that the conductive element is filiform instead of laminar.

Document GB-A-2 106 253 (FUJI) likewise describes an electrode for selectively determining ions, the electrode being a laminate comprising an insulating support, a conductive layer covered with an insoluble salt of the metal forming the conductive layer, and a hydrophobic layer of an ion selective material (ISM) covering the rest. This document also describes a simplified variant electrode omitting not only the reference electrode but also the insoluble salt. In this variant the electrode comprises only the conductive layer covered with ISM material. With regard to this kind of electrode, see also Anal. Chem. 44, 856 (1972).

Document US-A-4 454 007 (DUPONT) likewise describes a laminar ion selective electrode having the following structure: a baseplate of insulating material, a layer of conductive material, a layer comprising powdered carbon dispersed in a dielectric polymer, and finally an ion-selective diaphragm made of material which penetrates with the material in the preceding layer at their junction plane.

In conventional practice, the previously-described electrodes are used as follows: When testing a solution for analysis, a drop thereof is deposited on to the diaphragm, which has selective ion permeability, and the drop is also placed in contact with the external reference electrode, e.g. via a salt bridge, the terminals of the ion-selective electrode and the reference electrode being connected to a suitable electrometer for reading the potential. In numerous prior-art cases, the external reference electrode may be similar to or identical with the measuring electrode, and the external reference potential can be supplied either by a standard solution deposited simultaneously with the solution to be analyzed (in which case the solutions make contact by diffusion into a porous element situated between the deposition areas) or by a fixed reference element (the salt bridge for example) forming part of the external reference electrode.

In order to locate and fix the position of the drop of solution to be analyzed (and also the drop of standard solution when necessary) the ISM diaphragm is usually covered with a layer of insulating, waterproof material formed with compartments or windows giving access to only that portion of the ISM layer facing the window. This system prevents the drop spreading on the surface of the ISM layer and can also be used for selecting a fixed preset quantity of liquid for measuring, since the capacity of the compartments is kept constant from one electrode to the other.

The internal reference cell in laminar electrodes is a metal layer covered successively by an insoluble salt of the metal and a reference electrolyte having the same anion as the insoluble salt and the same cation as the ions to be selectively measured. These electrodes are valued for their stability and reliability, but it is often preferable, for simplicity of manufacture, to use electrodes where the reference cell is a redox system. In such cases, the reference element is simply a conductive layer (a metal or other conductive material such as graphite or carbon) covered by the redox system, usually embedded in a hydrophilic matrix. A wide variety of systems are used as the redox couple, e.g. $Fe^{+2}/Fe^{+3}$, quinhydrone, $Fe(CN)_6^{-3}/Fe(CN)_6^{-4}$, etc. However, if the reference element is to operate efficiently, it is usually necessary for the redox medium to be moistened, either before using the electrode (moist electrodes) or at the time of use (storage of electrodes when dry). Usually also, if the element is to have the optimum redox capacity, the molar ratio of the substance in oxidized form to the substance in reduced form must be near unity, which necessitates certain precautions during manufacture.

SUMMARY OF THE INVENTION

Attempts have therefore been made to simplify the manufacture of these electrodes by using novel redox systems, and this has been achieved by means of multilaminar dry, electrodes comprising an electric chemical reference cell that stable potential having a conductive base layer and a layer Prussian blue adhered firmly to the conductive base layer and a ion selective diaphragm which is selected for a specific ion to be detected, said ion selected diaphragm being deposited as a film on at least a portion of the layer of Prussian blue. The Prussian blue layer can be obtained in a very simple manner. It has a very stable potential, gives very reliable measurements and does not require any appreciable care regarding the relative proportions of components of the redox system. Also, the layer can be completely dry and does not require any binder.

BRIEF DESCRIPTION OF THE DRAWINGS

The invention will now be described in greater detail with reference to the accompanying drawings, in which.

DETAILED DESCRIPTION OF THE PREFERRED EMBODIMENTS

Figure 1:
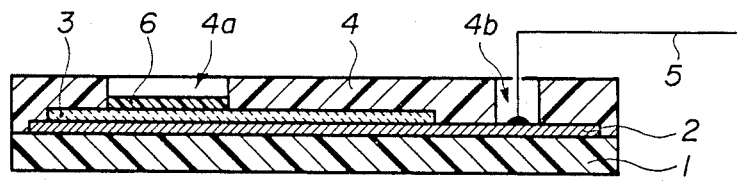
FIG. 1 is a diagrammatic section of an embodiment of the electrode constructed according to the invention.

FIG. 1 shows an electrode comprising the following elements in succession: an insulating base plate or sheet 1, an electrically conductive layer 2 cooperating with the next layer 3 to form a dry redox system, an internal reference cell at stable potential, and finally a mask 4 of insulating hydrophobic material covering the rest and formed with two windows 4a, 4b. Window 4b is for establishing electric contact, e.g. via a conductor 5 and consequently providing a contact zone for connecting layer 2 to a terminal of an electrometer (not shown).

The electrode, in intimate contact with the reference element 3, also comprises a diaphragm 6 selective for specific ions, e.g. K+ ions. The diaphragm is disposed in window 4a and secured in completely sealing-tight manner to the walls of the mask by solubilization and mutual interdiffusion between the binder of diaphragm 6 (a polymer) and the material of mask 4. This interpenetration results from the manufacturing process, details of which will be given hereinafter. However, this detail is limited to the present embodiment and is not connected with the nature of the internal reference electrode. Consequently, the distinctive feature of the invention, i.e. the layer of Prussian blue is of use for most of the applicable laminar electrode structures, including the known prior-art structures.

Figure 2:
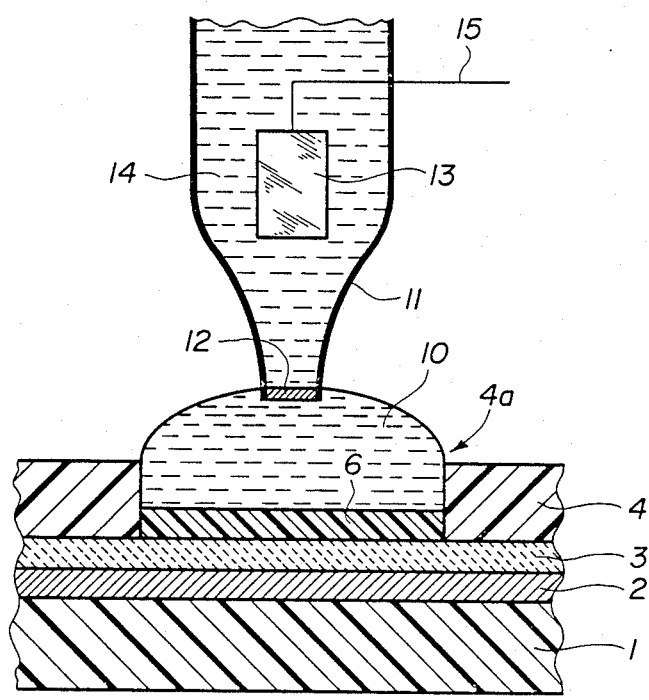
FIG. 2 is a larger-scale diagram of a method of measurement using an external reference electrode.

FIG. 2 illustrates one method of analyzing a solution 10 by means of the electrode in FIG. 1.

To make the analysis, a drop 10 of the solution for analysis is taken and deposited in the compartment 4a formed in mask 4, so that it makes contact with the ion selective diaphragm 6. Next, contact is made with an electrometer via a coupling means. e.g. a pipette 11 having a porous glass tip 12 and a reference electrode 13 (e.g. a silver plate covered with AgCl and immersed in a reference electrode 14, e.g. KCl N). Contact with the electrometer is made via conductor 5 and also via a conductor 15 connected to the reference electrode 13. Next, the potential of the electrochemical cell formed by the aforementioned elements is measured and if the internal reference potential (elements 2 and 3) and the concentration of the reference solution 14 are known it is possible to calculate the concentration of chosen ions in solution 10 by using the NERNST relation (see e.g. Ion-Selective Electrode Methodology by A. K. Covington, CRC Press Inc. (1984), Boca Raton, Fla.; "Physical Chemistry" by W. J. Moore, Prentice-Hall, Inc. 3e ed. London 1962, p.389).

The electrodes according to the invention can be constructed by using an insulating base 1 comprising a sheet film or plate of a polymer such as PVC. mylar, cellulose acetate, polycarbonates, plexiglass, polystyrene, etc. The nature of the insulating base is not critical provided it does not interfere with the other electrode components, and it can be made from conventional materials and by conventional methods.

The conductive layer 2 can be made from a metal sheet or film, e.g. Fe. Ag, Cu, Ni, Co, etc.. or carbon or fibres embedded in a polymer binder or a plate of vitreous carbon, or a sheet of porous carbon.

The layer of Prussian blue adhering to the conductive layer is obtained e.g. by immersing the conductive layer in a solution of $FeCl_3$ and subsequently in a solution of alkaline ferrocyanide. Alternatively the reverse method can be used. i.e. the conductive base can be successively contacted with the ferrocyanide and the ferric salt. The result, after drying is an adhesive Prussian blue layer having a thickness of about 0.01 to 10 $\mu m$ and a particularly stable potential (on an Fe, Ni, Co or carbon support). The layer does not require any binder and has a water content not exceeding 0.1%.

The mask 4 covering the electrode can be a hydrophobic polymer such as PVC,. Polyacrylate, polystyrene, polycarbonate etc. The mask can be a single adhesive polymer sheet pressed cold or hot on to the top part of the components of the laminate and intimately following their shape.

Diaphragm 6 comprises a binder, a plasticizer and an ionophore. The choice of ionophore will depend on the nature of the ions to be determined. e.g. valinomycin for potassium, methyl-monensin for sodium, certain phosphonic esters for calcium, etc. Detailed information on the required ionophores, depending on the chosen type of analysis, will be found among the previous citations inter alia document US-A-4 454 007.

Electrodes of the kind according to the invention may have defects due to short-circuits, either through inter-layer diffusion of the aqueous liquids for analysis, or when they accidentally come into contact with the edges of the electrodes. Attempts have been made to remedy these defects by various means, e.g. by tightly sealing the edges of the electrodes (GB-A-2 106 253) or by grooving the conductive edge so as to divide it into areas and filling the grooves with ISM material (GB-A 2 121 183).

As we shall show, in the manufacture of electrodes according to the invention, the short-circuit problem has been solved by a completely tight seal between the semi-permeable ion-selective (ISM) diaphragm and the impermeable hydrophobic mask covering the electrode.

The binder for the ionophoric compound can be a polymer such as polyvinyl chloride (PVC). polystyrene, polyacrylates. polycarbonates. Polyesters (Polyethylene terephthalate), etc. Preferably, to obtain optimum compatibility between member 6 and mask 4 (i.e. to ensure maximum sealing-tightness between these components) the polymer chosen for the binder of diaphragm 6 will be identical with the material in the mask, e.g. PVC. Also, in order to assemble the diaphragm, a solution of constituents thereof should be applied in a solvent in which the mask material is also soluble.

The plasticizer used in the diaphragm can be one of the conventional plasticizers such as dimethylphthalate, dioctylphenylphosphonate, dibutylphthalate, tritolylphosphate, dibutylsebacate, etc. Other examples of plasticizers will be found in the citations referred to.

The practical construction of the electrodes by the method according to the invention is simple and follows substantially from the preceding considerations.

The various laminate components are selected and superposed and joined either by simple adhesion or by pressing when cold or hot. For example, in one embodiment of an electrode as per FIG. 1 the method is as follows:

A conductive layer. e.g. a sheet of metal or coating of carbon (fibres or porous carbon) is deposited on to a plastics plate. The conductive layer is thoroughly cleaned and rinsed (since Prussian blue is extremely sensitive to traces of organic impurities) and a place of contact is formed at one end. A layer of ferric ferrocyanide is then deposited, chemically or electrolytically. After carefully rinsing the layer with water it is dried in the oven and kept in a desiccator. The electrode is completed by covering the assembly with an adhesive PVC mask formed with an opening corresponding to window 4a and an opening 4b for an electrical connection. The thickness of the mask is of the order of 0.05 to 0.5 mm. Next, a solution of ionophore containing PVC binder, a plasticizer and a solvent such as tetrahydroguran (THF) is deposited in the opening in the mask. The solution is then dried to form a film constituting the diaphragm 6. During this operation, the solvent dissolves part of the walls of the mask with which it is in contact and, after evaporation, forms a completely tight seal between the diaphragm and the walls of opening 4a.

The invention is illustrated by the following example.

EXAMPLE

A sheet of Fe, Ag, Ni, Pt or porous conductive carbon about 0.05 to 0.2 mm thick was selected and immersed for a few minutes in a hot non-ionic detergent.

The sheet was then repeatedly rinsed in hot distilled water. After a further rinse in twice distilled water, the sheet was dried for at least 4 hours at 150° C. The conductive sheet was handled with very great precautions (using metal forceps) to avoid depositing impurities.

A solution was also prepared of 20 mM $K_3Fe(CN)_6$, analytical grade, after twice being recrytallized from thrice-distilled water and acidified at 0.01M with HCl. The same method was used with, $FeCl_3$ and a corresponding 20 mM solution was prepared with 0.01M of HCl.

When the two solutions were carefully mixed, the mixture remained in unstable equilibrium; Prussian blue was not precipitated until later.

One of the conductive sheets was cathodized at 1 mA/cm$^2$ in 1 N HCl at 40° C. A sheet of Fe or Ni requires 5 minutes treatment whereas Pt takes about 60 minutes. A conductive carbon sheet does not require any cathodization.

The cathodized sheet was then rinsed in thrice-distilled water and slowly immersed in a freshly-prepared mixture of iron chloride solution and ferrocyanide solution except for a small Portion for subsequently forming an electric connection. After 5 minutes, a layer of Prussian blue formed on the conductive sheet. The coating continues to thicken if treatment is prolonged. The sheet was taken out of the bath after 5–20 minutes depending on the desired thickness, and carefully rinsed in thrice-distilled water and dried in the desiccator on $P_2O_5$.

Alternatively, deposition of Prussian blue can be accelerated by inserting a second sheet (of Platinum) into the mixture and applying a Potential between the sheets, the first being negatively Polarized so as to obtain a current density of 50 $\mu A/cm^2$. This method Provides a more uniform, homogeneous deposit than by Purely chemical deposition. A deposit of suitable thickness can be obtained by Passing about 10–15 mCoulombs/cm$^2$ per electrode.

After the sheet had been covered with Prussian blue, one surface of it was pressed against a self-adhesive protective film of polyethylene. PVC or mylar between 0.1 and 0.5 mm thick. A portion of sheet measuring approximately $7 \times 15$ mm was then cut, so that the Portion had an end zone not coated by the redox system, and of use for subsequently connecting the electrode to an electrometer.

The plate portion (except for the contact zone 4b) was then covered with a sheet of PVC (mask) formed (see FIG. 1) with an opening about 3 to 5 mm in diameter, giving access to a corresponding area of the active layer of the electrode. Mask 4 was made from a self-adhesive sheet about 0.1 mm in diameter.

About 20 $\mu l$ of an ISM solution prepared from 6.6 mg of valinomycin (Val); 2.014 mg of bis(2-ethylhexyl)adipate; 2.044 g of high molecular-weight PVC and 20 ml of tetrahydrofuran (THF) was then poured into window 4 through a pipette. The solution was then evaporated, during which time the THF dissolved Part of the PVC forming the Peripheral walls of the window, resulting in Penetration of the PVC binder into the walls of the mask and the ISM membrane. After drying, therefore, the membrane was intimately bonded to the mask walls by a completely water-tight junction zone.

The resulting electrodes were used as follows (see FIG. 2) Using a micropipette, a drop (20–50 l) of standard solution (or of solution to be measured) was placed in the compartment 4a in contact with the ISM diaphragm 6. Connector 5 was connected to the terminals of a high-impedance electrometer (differential preamplifier, input greater than $10^{-13}$ ohms, current approximately 2 pA, followed by Digital KEITHLEY-197 multimeter) and also to the external reference electrode, which comprised a sintered-tip micropipette in contact with the drop to be measured and containing a KCl reference solution and a plate of Ag/AgCl.

The test was made by measuring the potential every 6 seconds for a total Period of 6 minutes. In the Present example the electrodes stabilized quickly and had a very slight drift, below 0.1 mV/min. The results obtained on test KCl solutions containing $10^{-2}$ to $10^{-5}$M are shown in the following Table. These results relate to electrodes previously rinsed in distilled water and then with the solution to be measured at each change in concentration.

| Electrode No. | Conductive base | Measurement (mV) Conc.Sol.KCl (molarity) | | | | Linearity range (M) |
|---|---|---|---|---|---|---|
| | | $10^{-5}$ | $10^{-4}$ | $10^{-3}$ | $10^{-2}$ | |
| PB-1 | C porous | 365 | 393 | 443 | 497 | $10^{-2}-10^{-4}$ |
| PB-2 | Ni (Fe)* | 128 | 122 | 162 | 201 | $10^{-2}-10^{-4}$ |
| PB-3 | C fibres | 167 | 208 | 254 | 304 | $10^{-2}-10^{-4}$ |

*Nickel-plated iron

Figure 3:
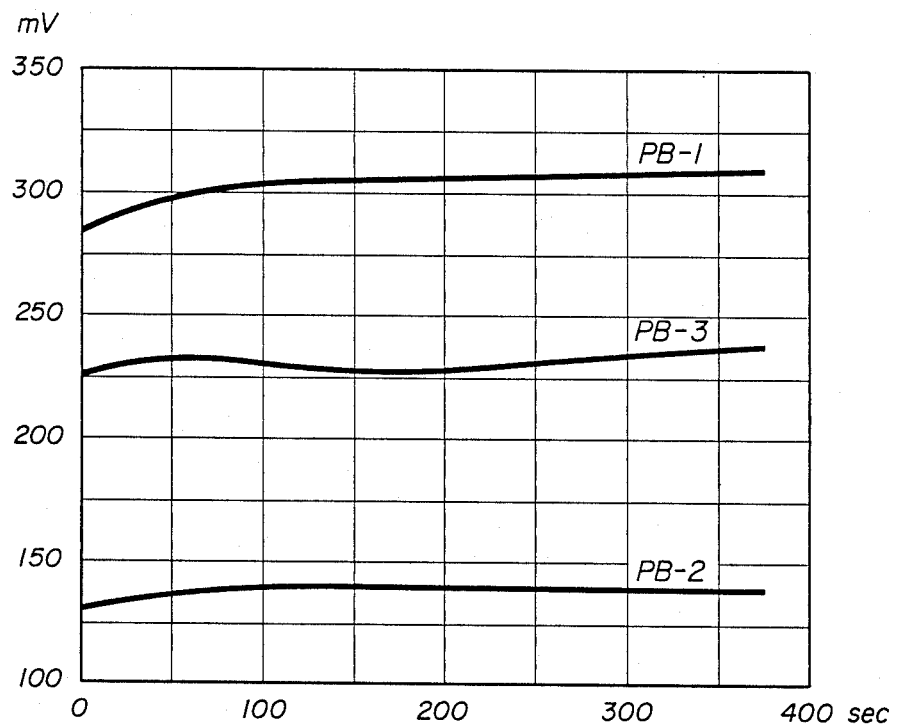
FIG. 3 is a graph showing the variation in time of the potential of the electrodes according to the invention during the stabilization period.

The stability of the aforementioned electrodes was very satisfactory. After they had stabilized. the potential drift did not exceed + or −0.2 mV/min. Stabilization took about 2 minutes (see FIG. 3).

While the invention has been described in conjunction with certain embodiments, it is understood that various modifications and changes may be made without departing from the spirit and scope of the invention.

We claim:

1. A multilaminar dry electrode for determining the concentration of a specific ion in an aqueous solution, such as biological fluid, comprising:
   (a) an electrochemical reference cell at stable potential having a conductive base layer and a layer of Prussian blue adhered firmly to the conductive base layer; and
   (b) an ion selective diaphragm which is selected for the specific ion to be detected said ion selective diaphragm being deposited as a film on at least a Portion of the layer of Prussian blue;
   whereby, when a drop of aqueous solution containing the specific ion to be detected is placed on the ion selective diaphragm and an external electrode is electrically interconnected with the diaphragm by the aqueous solution a concentration of the ion to be detected in the drop of aqueous solution may be determined by measuring an electrical potential between the electrochemical reference cell and the external electrode without the multilaminar dry electrode requiring any pre-treatment.

2. A multilaminar dry electrode according to claim 1, wherein the thickness of the Prussian blue layer is more than 0.01 $\mu$.

3. A multilaminar dry electrode according to claim 1, further comprising means for stabilizing the Potential drift of said multilaminar dry electrode such that the Potential drift after two minutes of stabilization does not exceed ±0.2 mV-min.

4. A multilaminar dry electrode according to claim 1, wherein the Prussian blue layer is dry, and has a water content not exceeding 0.1%.

* * * * *